(12) United States Patent
Thornton

(10) Patent No.: US 7,007,698 B2
(45) Date of Patent: Mar. 7, 2006

(54) BODY LUMEN CLOSURE

(75) Inventor: Sally C. Thornton, Marlborough, MA (US)

(73) Assignee: Boston Scientific Corporation, Natick, MA (US)

( * ) Notice: Subject to any disclaimer, the term of this patent is extended or adjusted under 35 U.S.C. 154(b) by 243 days.

(21) Appl. No.: 10/115,552

(22) Filed: Apr. 3, 2002

(65) Prior Publication Data

US 2003/0191479 A1    Oct. 9, 2003

(51) Int. Cl.
*A61B 19/00* (2006.01)

(52) U.S. Cl. ............................. 128/898; 606/228
(58) Field of Classification Search ............. 128/898; 606/228
See application file for complete search history.

(56) References Cited

U.S. PATENT DOCUMENTS

| | | | |
|---|---|---|---|
| 3,716,058 A * | 2/1973 | Tanner, Jr. ................ 606/221 |
| 4,170,990 A * | 10/1979 | Baumgart et al. ........... 606/78 |
| 4,512,338 A * | 4/1985 | Balko et al. ................ 606/108 |
| 4,580,568 A | 4/1986 | Gianturco |
| 4,872,874 A | 10/1989 | Taheri |
| 4,904,254 A | 2/1990 | Lane |
| 5,002,563 A * | 3/1991 | Pyka et al. ................ 606/222 |
| 5,147,389 A | 9/1992 | Lane |
| 5,330,503 A * | 7/1994 | Yoon ......................... 606/223 |
| 5,476,471 A | 12/1995 | Shifrin et al. |
| 5,582,616 A * | 12/1996 | Bolduc et al. ............. 606/143 |
| 5,601,572 A * | 2/1997 | Middleman et al. ....... 606/139 |
| 5,769,780 A | 6/1998 | Hata et al. |
| 5,810,847 A | 9/1998 | Laufer et al. |
| 5,810,882 A * | 9/1998 | Bolduc et al. ............. 606/213 |
| 5,824,008 A * | 10/1998 | Bolduc et al. ............. 606/143 |
| 5,957,949 A | 9/1999 | Leonhardt et al. |
| 5,964,772 A * | 10/1999 | Bolduc et al. ............. 606/142 |
| 5,989,268 A * | 11/1999 | Pugsley et al. ............ 606/144 |
| 6,059,800 A | 5/2000 | Hart et al. |
| 6,241,763 B1 | 6/2001 | Drasler et al. |
| 6,269,819 B1 | 8/2001 | Oz et al. |
| 6,287,317 B1 | 9/2001 | Makower et al. |
| 6,666,885 B1 | 12/2003 | Moe ........................ 623/2.12 |
| 6,666,886 B1 | 12/2003 | Tranquillo et al. ........ 623/2.42 |
| 6,669,725 B1 | 12/2003 | Scott ....................... 623/2.36 |
| 6,673,109 B1 | 1/2004 | Cox ......................... 623/2.12 |
| 6,676,698 B1 | 1/2004 | McGuckin, Jr. et al. ... 623/1.24 |
| 6,676,702 B1 | 1/2004 | Mathis ..................... 623/2.36 |
| 6,682,558 B1 | 1/2004 | Tu et al. ................... 623/2.11 |
| 6,682,559 B1 | 1/2004 | Myers et al. .............. 623/2.13 |

(Continued)

FOREIGN PATENT DOCUMENTS

WO    WO 99/04724    2/1999

(Continued)

OTHER PUBLICATIONS

US 6,673,110, 01/2004, Alfieri et al. (withdrawn)

(Continued)

*Primary Examiner*—Gary Jackson
(74) *Attorney, Agent, or Firm*—Brooks & Cameron, PLLC

(57) ABSTRACT

Method and apparatus implementing and using techniques for body lumen closure, including use of an implantable medical closure device. The device includes a flexible strand defining an arcuate form. The strand is deformable upon implantation from a large cross-section condition to a small cross-section condition and has at least two anchoring portions disposed along the strand. The anchoring portions are configured to penetrate a wall of a body lumen such that when the strand is deformed to the small cross-section condition, the wall of the body lumen is disposed inwardly.

16 Claims, 14 Drawing Sheets

U.S. PATENT DOCUMENTS

| | | | |
|---|---|---|---|
| 6,685,739 B1 | 2/2004 | DiMatteo et al. | 623/1.24 |
| 6,692,512 B1 | 2/2004 | Jang | 606/200 |
| 6,695,878 B1 | 2/2004 | McGuckin, Jr. et al. | 623/1.19 |
| 6,695,886 B1 | 2/2004 | Brown et al. | 606/213 |
| 6,709,456 B1 | 3/2004 | Langberg et al. | 623/2.37 |
| 6,709,457 B1 | 3/2004 | Otte et al. | 623/2.4 |
| 6,716,241 B1 | 4/2004 | Wilder et al. | 623/1.24 |
| 6,716,244 B1 | 4/2004 | Wilder et al. | 623/1.24 |
| 6,719,767 B1 | 4/2004 | Kimblad | 606/151 |
| 6,719,784 B1 | 4/2004 | Henderson | 623/1.44 |
| 6,719,786 B1 | 4/2004 | Ryan et al. | 623/2.11 |
| 6,719,787 B1 | 4/2004 | Cox | 623/2.12 |
| 6,719,788 B1 | 4/2004 | Cox | 623/2.12 |
| 6,719,789 B1 | 4/2004 | Cox | 623/2.13 |
| 6,719,790 B1 | 4/2004 | Brendzel et al. | 623/2.4 |
| 6,723,038 B1 | 4/2004 | Schroeder et al. | 600/16 |
| 6,723,122 B1 | 4/2004 | Yang et al. | 623/2.1 |
| 6,723,123 B1 | 4/2004 | Kazatchkov et al. | 623/2.2 |
| 6,726,715 B1 | 4/2004 | Sutherland | 623/2.1 |
| 6,726,716 B1 | 4/2004 | Kazatchkov et al. | 623/2.36 |
| 6,726,717 B1 | 4/2004 | Alfieri et al. | 623/2.36 |
| 6,730,118 B1 | 5/2004 | Spenser et al. | 623/1.24 |
| 6,730,121 B1 | 5/2004 | Ortiz et al. | 623/2.17 |
| 6,730,122 B1 | 5/2004 | Ortiz et al. | 623/2.33 |
| 6,736,845 B1 | 5/2004 | Marquez et al. | 623/2.11 |
| 6,736,846 B1 | 5/2004 | Cox | 623/2.12 |
| 6,749,630 B1 | 6/2004 | McCarthy et al. | 623/2.36 |
| 6,752,813 B1 | 6/2004 | Goldfarb et al. | 606/139 |
| 6,752,828 B1 | 6/2004 | Thornton | 623/1.24 |
| 6,755,857 B1 | 6/2004 | Peterson et al. | 623/2.17 |
| 6,761,734 B1 | 7/2004 | Suhr | 623/1.35 |
| 6,761,735 B1 | 7/2004 | Eberhardt et al. | 623/2.1 |
| 6,764,494 B1 | 7/2004 | Menz et al. | 606/159 |
| 6,764,508 B1 | 7/2004 | Roehe et al. | 623/2.11 |
| 6,764,509 B1 | 7/2004 | Chinn et al. | 623/2.12 |
| 6,764,510 B1 | 7/2004 | Vidlund et al. | 623/2.34 |
| 6,767,362 B1 | 7/2004 | Schreck | 623/2.11 |
| 6,769,434 B1 | 8/2004 | Liddicoat et al. | 128/898 |
| 6,770,083 B1 | 8/2004 | Seguin | 606/142 |
| 6,780,200 B1 | 8/2004 | Jansen | 623/2.17 |
| 6,786,924 B1 | 9/2004 | Ryan et al. | 623/2.36 |
| 6,786,925 B1 | 9/2004 | Buchanan et al. | 623/2.36 |
| 6,790,229 B1 | 9/2004 | Berreklouw | 623/2.1 |
| 6,790,230 B1 | 9/2004 | Beyersdorf et al. | 623/2.18 |
| 6,790,231 B1 | 9/2004 | Liddicoat et al. | 623/2.37 |
| 6,793,673 B1 | 9/2004 | Kowalsky et al. | 623/2.36 |
| 6,797,000 B1 | 9/2004 | Simpson et al. | 623/2.15 |
| 6,797,001 B1 | 9/2004 | Mathis et al. | 623/2.37 |
| 6,797,002 B1 | 9/2004 | Spence et al. | 623/2.38 |
| 6,802,860 B1 | 10/2004 | Cosgrove et al. | 623/2.11 |
| 6,805,710 B1 | 10/2004 | Bolling et al. | 623/2.36 |
| 6,805,711 B1 | 10/2004 | Quijano et al. | 623/2.37 |
| 6,810,882 B1 | 11/2004 | Langberg et al. | 128/898 |
| 6,821,297 B1 | 11/2004 | Snyders | 623/2.18 |
| 6,824,562 B1 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B1 | 1/2005 | Nguyen et al. | 623/2.13 |
| 6,840,246 B1 | 1/2005 | Downing | 128/898 |
| 6,840,957 B1 | 1/2005 | DiMatteo et al. | 623/1.24 |
| 6,846,324 B1 | 1/2005 | Stobie | 623/2.11 |
| 6,846,325 B1 | 1/2005 | Liddicoat | 623/2.4 |
| 6,858,039 B1 | 2/2005 | McCarthy | 623/2.36 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.12 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |
| 2004/0148020 A1 | 7/2004 | Vidlund et al. | 623/2.36 |

| Publication | Date | Inventor | Class |
|---|---|---|---|
| 2004/0153052 A1 | 8/2004 | Mathis | 606/1 |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Keuhn et al. | 606/108 |
| 2004/0167610 A1 | 8/2004 | Ortiz et al. | 623/2.11 |
| 2004/0172046 A1 | 9/2004 | Hlavka et al. | 606/142 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/108 |
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Iobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193191 A1 | 9/2004 | Starksen et al. | 606/153 |
| 2004/0193253 A1 | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/1.24 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | 623/2.17 |
| 2004/0210307 A1 | 10/2004 | Khairkhahan | 623/2.18 |
| 2004/0215333 A1 | 10/2004 | Duran et al. | 623/1.24 |
| 2004/0215339 A1 | 10/2004 | Drasler et al. | 623/3.1 |
| 2004/0220654 A1 | 11/2004 | Mathis et al. | 623/1.11 |
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1 | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |
| 2004/0236411 A1 | 11/2004 | Sarac et al. | 623/1.26 |
| 2004/0236418 A1 | 11/2004 | Stevens | 623/2.11 |
| 2004/0236419 A1 | 11/2004 | Milo | 623/2.36 |
| 2004/0243153 A1 | 12/2004 | Liddicoat et al. | 606/151 |
| 2004/0243219 A1 | 12/2004 | Fischer et al. | 623/1.15 |
| 2004/0243227 A1 | 12/2004 | Starksen et al. | 623/2.11 |
| 2004/0243228 A1 | 12/2004 | Kowalsky et al. | 623/2.11 |
| 2004/0243230 A1 | 12/2004 | Navia et al. | 623/2.36 |
| 2004/0249452 A1 | 12/2004 | Adams et al. | 623/2.36 |
| 2004/0254600 A1 | 12/2004 | Zarbatany et al. | 606/194 |
| 2004/0254636 A1 | 12/2004 | Flagle et al. | 623/1.24 |
| 2004/0260276 A1 | 12/2004 | Rudko et al. | 606/15 |
| 2004/0260317 A1 | 12/2004 | Bloom et al. | 606/151 |
| 2004/0260322 A1 | 12/2004 | Rudko et al. | 606/167 |
| 2004/0260389 A1 | 12/2004 | Case et al. | 623/1.24 |
| 2004/0260390 A1 | 12/2004 | Sarac et al. | 623/1.24 |
| 2004/0260393 A1 | 12/2004 | Rahdert et al. | 623/2.36 |
| 2004/0260394 A1 | 12/2004 | Douk et al. | 623/2.36 |
| 2004/0267357 A1 | 12/2004 | Allen et al. | 623/2.11 |
| 2005/0004583 A1 | 1/2005 | Oz et al. | 606/142 |
| 2005/0004667 A1 | 1/2005 | Swinford et al. | 623/2.36 |
| 2005/0010285 A1 | 1/2005 | Lambrecht et al. | 623/2.18 |
| 2005/0010287 A1 | 1/2005 | Macoviak et al. | 623/2.36 |
| 2005/0015112 A1 | 1/2005 | Cohn et al. | 606/200 |
| 2005/0021056 A1 | 1/2005 | St. Goar et al. | 606/144 |
| 2005/0021136 A1 | 1/2005 | Xie et al. | 623/2.14 |
| 2005/0027261 A1 | 2/2005 | Weaver et al. | 604/246 |
| 2005/0027348 A1 | 2/2005 | Case et al. | 623/1.24 |
| 2005/0027351 A1 | 2/2005 | Reuter et al. | 623/2.11 |
| 2005/0027353 A1 | 2/2005 | Alferness et al. | 623/2.11 |
| 2005/0033398 A1 | 2/2005 | Seguin | 623/1.11 |
| 2005/0033419 A1 | 2/2005 | Alferness et al. | 623/2.11 |
| 2005/0033446 A1 | 2/2005 | Deem et al. | 623/23.6 |
| 2005/0038506 A1 | 2/2005 | Webler et al. | 623/2.11 |
| 2005/0038507 A1 | 2/2005 | Alferness et al. | 623/2.11 |
| 2005/0043790 A1 | 2/2005 | Seguin | 623/2.18 |
| 2005/0043792 A1 | 2/2005 | Solem et al. | 623/2.36 |

FOREIGN PATENT DOCUMENTS

| | | |
|---|---|---|
| WO | WO 01/54625 A1 | 8/2001 |
| WO | WO 2004019825 | 3/2004 |
| WO | WO 2004021893 | 3/2004 |
| WO | WO 2004023980 | 3/2004 |
| WO | WO 2004/032724 | 4/2004 |
| WO | WO 2004/032796 | 4/2004 |
| WO | WO 2004030568 | 4/2004 |
| WO | WO 2004030569 | 4/2004 |
| WO | WO 2004030570 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/047677 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |
| WO | WO2004/075789 | 9/2004 |
| WO | WO2004/080352 | 9/2004 |
| WO | WO2004/082523 | 9/2004 |
| WO | WO2004/082527 | 9/2004 |
| WO | WO2004/082528 | 9/2004 |
| WO | WO2004/082536 | 9/2004 |
| WO | WO2004/082537 | 9/2004 |
| WO | WO2004/082538 | 9/2004 |
| WO | WO2004/082757 | 9/2004 |
| WO | WO 2004/084746 | 10/2004 |
| WO | WO 2004/084770 | 10/2004 |
| WO | WO 2004/089246 | 10/2004 |
| WO | WO 2004/089250 | 10/2004 |
| WO | WO 2004/089253 | 10/2004 |
| WO | WO 2004/091449 | 10/2004 |
| WO | WO 2004/091454 | 10/2004 |
| WO | WO 2004/093638 | 11/2004 |
| WO | WO 2004/093726 | 11/2004 |
| WO | WO 2004/093728 | 11/2004 |
| WO | WO 2004/093730 | 11/2004 |
| WO | WO 2004/093745 | 11/2004 |
| WO | WO 2004/093935 | 11/2004 |
| WO | WO 2004/096100 | 11/2004 |
| WO | WO 2004/103222 | 12/2004 |
| WO | WO 2004/103223 | 12/2004 |
| WO | WO 2004/105584 | 12/2004 |
| WO | WO 2004/105651 | 12/2004 |
| WO | WO 2004/112582 | 12/2004 |
| WO | WO 2004/112585 | 12/2004 |
| WO | WO 2004/112643 | 12/2004 |
| WO | WO 2004/112652 | 12/2004 |
| WO | WO 2004/112657 | 12/2004 |
| WO | WO 2004/112658 | 12/2004 |
| WO | WO 2005/000152 | 1/2005 |
| WO | WO 2005/002424 | 1/2005 |

| WO | WO 2005/002466 | 1/2005 |
| WO | WO 2005/004753 | 1/2005 |
| WO | WO 2005/007017 | 1/2005 |
| WO | WO 2005/007018 | 1/2005 |
| WO | WO 2005/007036 | 1/2005 |
| WO | WO 2005/007037 | 1/2005 |
| WO | WO 2005/009285 | 2/2005 |
| WO | WO 2005/009286 | 2/2005 |
| WO | WO 2005/009505 | 2/2005 |
| WO | WO 2005/009506 | 2/2005 |
| WO | WO 2005/011473 | 2/2005 |
| WO | WO 2005/011534 | 2/2005 |
| WO | WO 2005/011535 | 2/2005 |
| WO | WO 2005/013860 | 2/2005 |

OTHER PUBLICATIONS

US 6,723,117, 04/2004, Menz et al. (withdrawn)

* cited by examiner

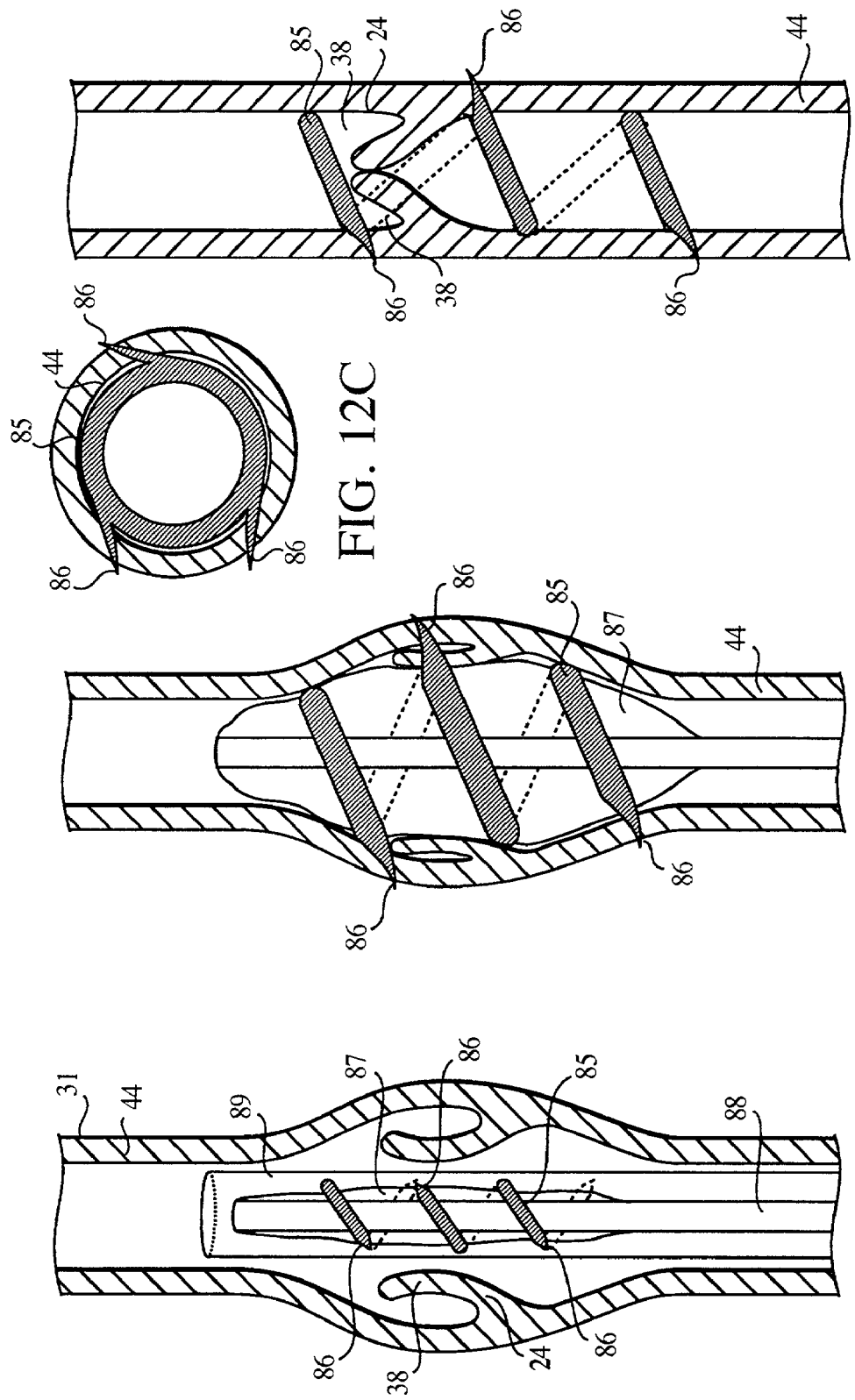

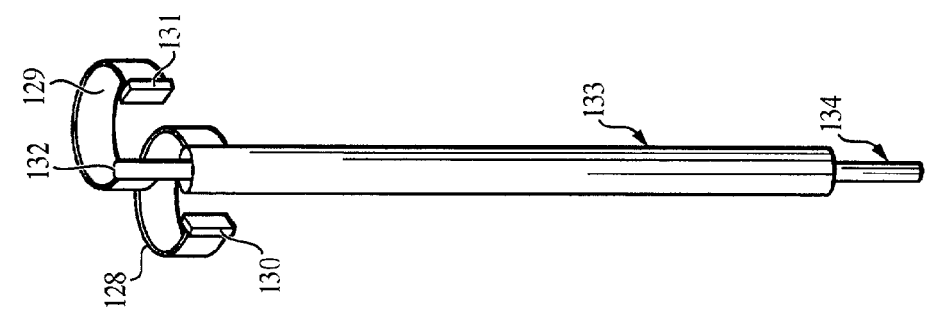
FIG. 15C
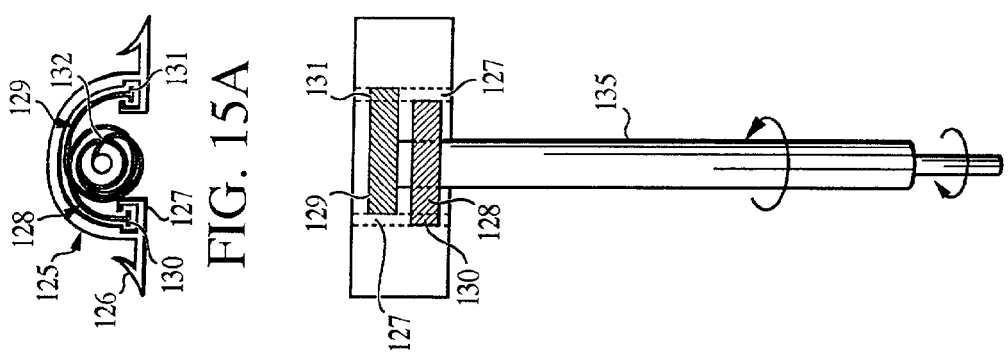
FIG. 15A
FIG. 15B

BODY LUMEN CLOSURE

TECHNICAL FIELD

This invention relates to body lumen closure.

BACKGROUND

A venous valve functions to prevent retrograde flow of blood and allow only antegrade flow of blood to the heart. Referring to FIG. 1A, a healthy venous valve 12 is illustrated in a vessel 10. The valve is bicuspid, with opposed cusps 14. In the closed condition, the cusps 14 are drawn together to prevent retrograde flow (arrow 16) of blood. Referring to FIG. 1B, if the valve is incompetent, the cusps 14 do not seal properly and retrograde flow of blood occurs. Incompetence of a venous valve is thought to arise from at least the following two medical conditions: varicose veins and chronic venous insufficiency.

SUMMARY

In a first aspect, the invention features an implantable medical closure device. The device includes a flexible strand defining an arcuate form. The strand is deformable upon implantation from a large cross-section condition to a small cross-section condition and has at least two anchoring portions disposed along the strand. The anchoring portions are configured to penetrate a wall of a body lumen such that when the strand is deformed to the small cross-section condition, the wall of the body lumen is disposed inwardly.

The strand can also be deformable from a second small cross-section condition to the large cross-section condition, for example, the strand may be deformed to the second small cross-section condition to facilitate delivery of the strand to a treatment site, where it is then deformed to the large cross-section condition upon implementation. The strand can include free ends, which free ends can include the anchoring portions of the strand. The strand can define an arc, a helix or can include linear leg portions. The strand can be a filament-form or a band and may be corrugated. The strand can deform from the large cross-section condition to the small cross-section condition by, for example, elastic recovery forces or thermal shape-memory effect. The strand can be formed of metal, for example, nitinol. The anchoring portions of the strand can include, for example, a loop or a barb.

In another aspect, the invention features a catheter system, which system includes a catheter for delivery into a lumen. The catheter includes an expander that can be operated between a small cross-section and a large cross-section. The catheter system also includes a closure device positioned about the expander. The closure device is a strand defining an arcuate form and including at least two anchoring portions configured to penetrate a wall of a body lumen. The closure device is deformable by the expander from a first small cross-section condition to a larger cross-section condition to dispose the closure device into engagement with the lumen wall. The closure device is further deformable to a second small cross-section condition, so that the wall of the body lumen is disposed inwardly.

The expander can take any convenient form, including, for example, an inflatable balloon, a mechanical expander or a leveraging device. The mechanical expander can include a two-part axial member having a first inner part connected to a first coiled spring and a second outer part connected to a second coiled spring. The closure device is mounted on the first and second coiled springs, and the first inner part of the axial member is rotatable to expand the first coiled spring and the second outer part of the axial member is rotatable to expand the second coiled spring. Expansion of the first and second coiled springs expands the closure device. Each coiled spring can include a distal end configured to fit within a groove formed on either end of the closure device.

The leveraging device can include a two-part axial member including a first outer part and a second inner part. A splayed cuff is connected to the distal end of the first outer part of the two-part axial member, and at least two flexible legs are connected to the distal end of the second inner part of the two-part axial member. The legs are flared outwardly to contact the distal end of the splayed cuff. The second inner part of the two-part axial member is moveable toward the splayed cuff such that the flexible legs and the splayed cuff expand radially. The closure device is positioned about the flexible legs and expansion of the flexible legs expands the closure device from a first small cross-section condition to a larger cross-section condition. The second inner part of the two-part axial member is also moveable away from the splayed cuff such that the flexible legs and the splayed cuff retract.

In another aspect, the invention features a method of treating a body lumen. The method includes delivering a closure device into a lumen and positioning the strand about the lumen such that a portion of the strand penetrates the wall of the lumen. The method further includes deforming the strand to a smaller cross-section condition such that the wall of the lumen is disposed inwardly. The strand can be positioned about the lumen such that an end of the strand extends through the wall of the lumen. The strand can be disposed on a catheter, which catheter is then delivered into the lumen. The catheter can include an expansion member.

Embodiments may have one or more of the following advantages. Closure of a body lumen can be achieved in a minimally invasive manner by delivery of a closure device to a treatment site using a catheter. The closure device may be partially installed within the lumen but configured to minimize profile and thus reduce impedance to the flow of body fluids through the lumen. The amount of lumen closure can be controlled by selecting the size and/or recovery force of the closure device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a cross-sectional schematic of a vessel including a competent venous valve while

FIG. 2A is a longitudinal cross section of a vessel including a closure device, while

FIGS. 12A, 12B, and 12D are longitudinal cross-sectional schematic views and FIG. 12C is a radial cross-sectional schematic view illustrating implantation of a closure device from within a vessel.

FIGS. 15A, 15B and 15C are schematic views of an embodiment of a medical device.

Like reference symbols in the various drawings indicate like elements.

DETAILED DESCRIPTION

Figure 1A:
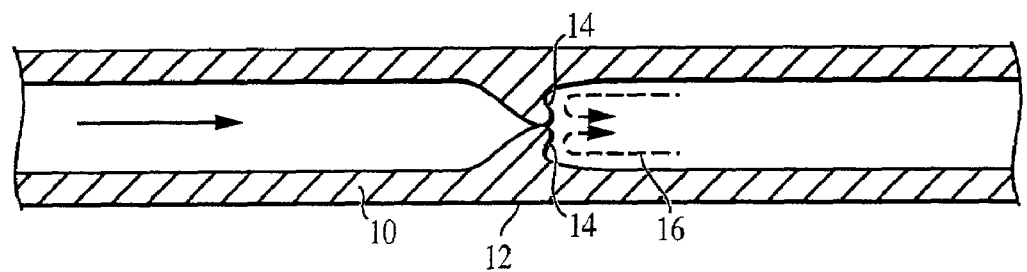
Figure 1B:
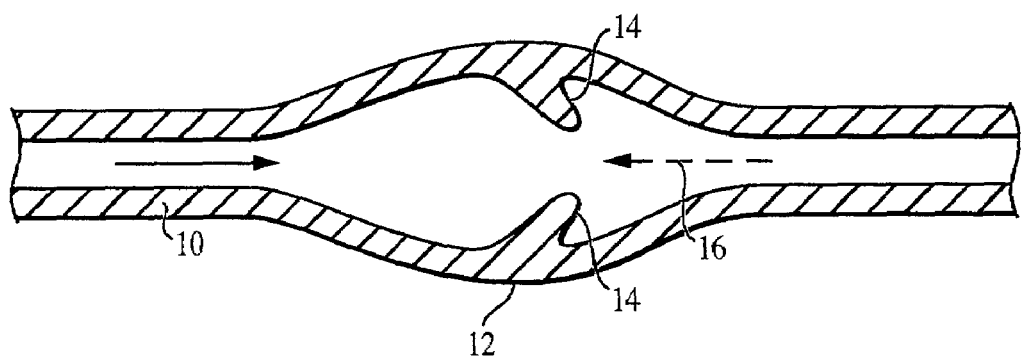
FIG. 1B is a schematic of a vessel including an in competent venous valve.
Figure 2A:
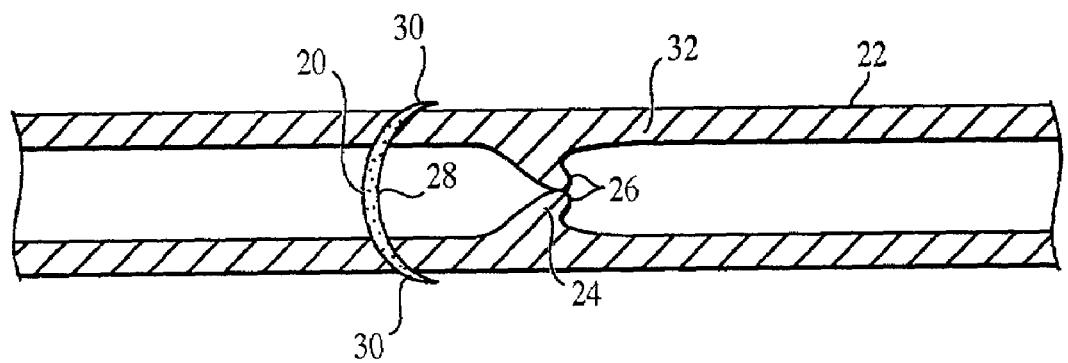
Figure 2B:
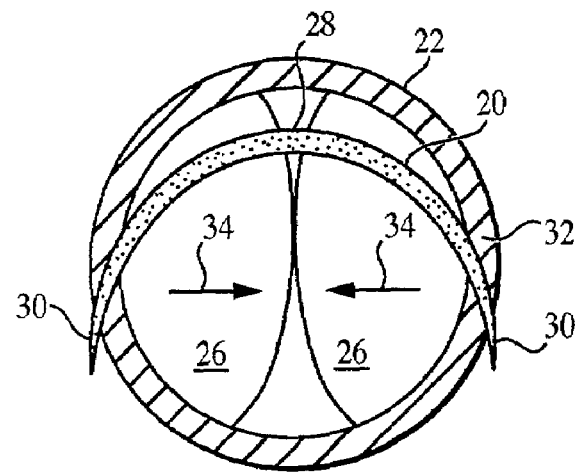
FIG. 2B is a radial cross section of the vessel including the closure device.

Referring to FIGS. 2A and 2B, a valve closure device 20 is illustrated in position about a vessel 22 at the location of a valve 24 including cusps 26. The closure device 20 is an arcuate, open-ended, filament-form defining an arc that includes a body 28 which is located in the lumen of the vessel and two anchoring portions 30 which extend into the walls 32 of the vessel. The device 20 provides a force (arrows 34) that draws the vessel walls inward, enhancing the function of the valve 24. As evident, the closure device 20 does not substantially impede the flow of blood through the vessel. The body portion 30 is thin and conforms closely to the vessel wall, outside of central portions of the vessel, where flow volume and rate is greatest.

Figure 3A:
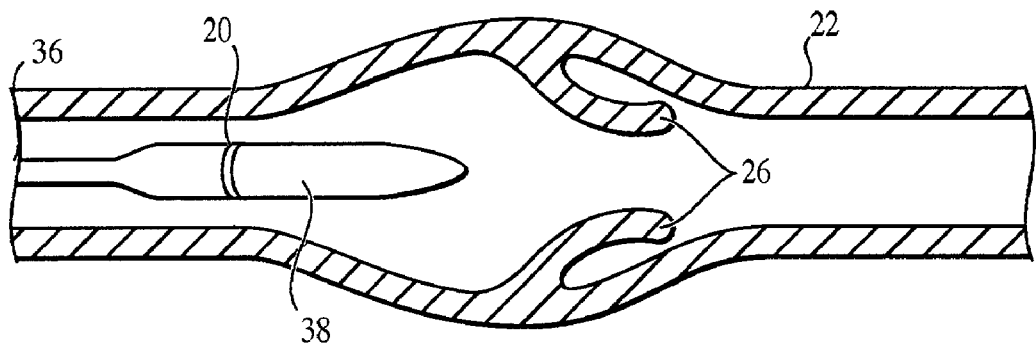
FIGS. 3A and 3B are longitudinal and radial cross-sectional views, respectively, illustrating delivery of a closure device using a catheter.
Figure 3B:
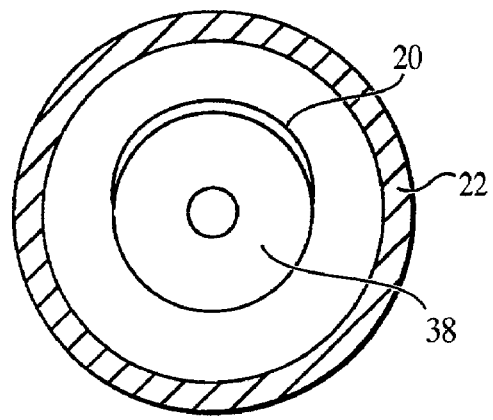

Referring to FIGS. 3A and 3B, the closure device 20 can be positioned at a treatment site in vessel 22 using a catheter 36, which may be delivered into the vessel percutaneously. The catheter 36 includes a long, flexible body adapted for delivery through the vessel and has near its distal end an expander 38, such as an inflatable balloon. Suitable balloon catheters include angioplasty balloon catheters and balloon catheters adapted for delivering stents. An example utilizing a coextruded balloon is described in Hamilton et al., U.S. Pat. No. 5,797,877, the entire contents of which is incorporated herein by reference. The catheter may be delivered over a guidewire (not shown). The device 20 may be friction fit over the catheter. A retractable sheath may be used to cover the device and balloon during delivery.

Figure 4A:
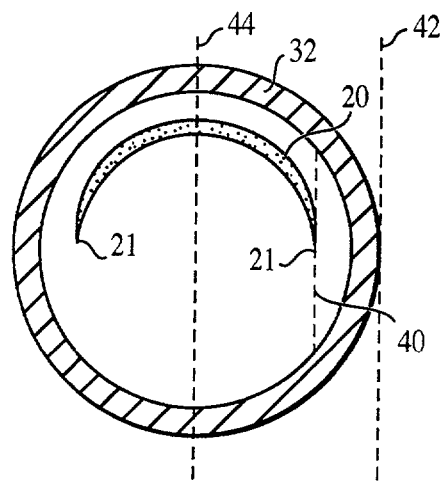
FIGS. 4A, 4B and 4C are radial cross-sectional views illustrating implantation of a closure device from within a vessel.
Figure 4B:
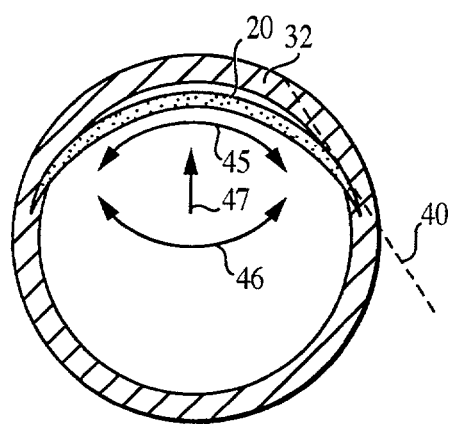
Figure 4C:
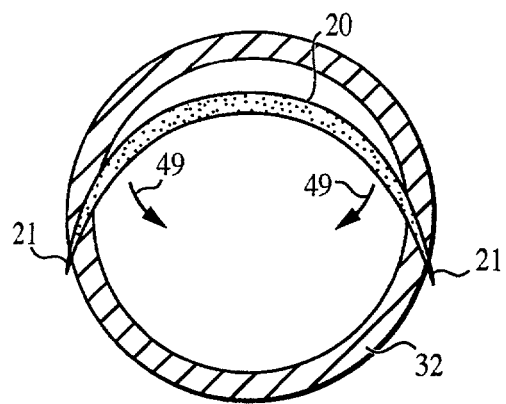

The closure device 20, in a radially compacted form, is positioned over the expander 38 in a deflated condition for delivery to the treatment site. Referring as well to FIGS. 4A–4C, the closure device 20 is installed at the treatment site by expanding the expander 38, i.e. by inflating the balloon. (In FIGS. 4A–4C, the expander and valve cusps are omitted to more clearly illustrate the installation of the closure device 32). Referring particularly to FIG. 4A, the closure device 20 is in a compacted condition as it is carried to the treatment site on the catheter, with the expander in the unexpanded condition. The closure device 20 is sized such that it is smaller than the cross-section of the vessel. In the embodiment illustrated, the closure device 20 defines an arc that is generally concentric with the arc defined by the vessel wall. In this condition, the anchoring portions 30 terminate in ends 21 which are oriented along a line 40, substantially parallel to the center line 44 through the cross-section of the vessel and generally parallel to a tangent 42, on the blood vessel wall 32. Referring particularly to FIG. 4B, as the closure device 20 is expanded, the device can both stretch axially (arrow 45) and deform radially (arrow 46) as well as be displaced upwardly (arrow 47). The axial stretching does not fully accommodate the expansion. As a result, the ends of the filament are deflected such that they are oriented along line 40, and come into contact with the vessel wall 32, such that the ends become embedded in the wall. The initial penetration of the ends can be enhanced by rotating the catheter slightly about the catheter axis. Referring to FIG. 4C, as the expander is contracted (i.e. deflated) device 30 begins to contract. The ends 21 further penetrate the wall 32. As shown the ends may pierce the entire thickness of the wall, and deflect inwardly (arrow 49) to contract the vessel. The closure device can be deployed near the base of cusps of an incompetent venous valve, where the cusps meet the wall of the blood vessel. The deployment may be upstream of the cusps. Alternatively, the deployment site can be downstream of the cusps. The catheter is withdrawn through the blood vessel in the same manner the catheter was initially inserted.

The closure device may be made of a thin elongate, filament form, such as a metal wire. The metal may be selected such that the device is elastically expandable from the compacted condition for delivery into a lumen to an expanded condition for implantation. Once implanted, elastic recovery of the wire contracts the device and the vessel wall. Suitable metals include elastic steels and superelastic alloy materials such as nitinol. The filament may also be a composite material, such as a composite wire. Superelastic metals and composite wires are described in Heath, U.S. Pat. No. 5,725,570, and Mayer, U.S. Pat. No. 5,800,511, the entire contents of both of which are incorporated herein by reference. The metal may also be a temperature-effect shape memory superelastic alloy that conforms to an implanted condition upon exposure to a controlled temperature, e.g. body temperature. Suitable shape memory alloys such as nitinol are discussed in Schetsky MacDonald "Shape Memory Alloys," Encyclopedia of Chemical Technology ($3^{rd}$ ed) John Wiley and Sons, 1982, vol. 20, p. 726–736. The temperature of the device may be controlled, for example, by heating the expander or by heating the balloon inflation fluid. The wire may also be selected such that the device is plastically deformed from the compacted condition to an expanded condition for embedding the anchoring elements into the vessel wall, with some elastic recovery after the expansion to contract the wall. Alternatively, a mechanical gripper can be used to draw the anchoring portions inward. The filament may also be made of a flexible polymer. The device may be coated with a lubricious polymer or a drug. For example, the anchoring portions may include a tissue sealant to minimize bleeding and enhance vessel wall integrity in the penetration regions.

The anchoring portions can also take a number of different forms that permit the ends of the closure device to penetrate the wall of the blood vessel, and restrain the ends from re-entering the vessel. In the embodiment illustrated above, the device 20 is formed of an open-ended strand in the shape of an arc. This shape facilitates deflection of the ends of the strand so that they can be embedded in the vessel wall and also provides a small profile within the vessel, so that blood flow is not substantially impeded. As illustrated above, the body of the device, within the vessel, closely conforms to the inner wall of the lumen.

Figure 5:
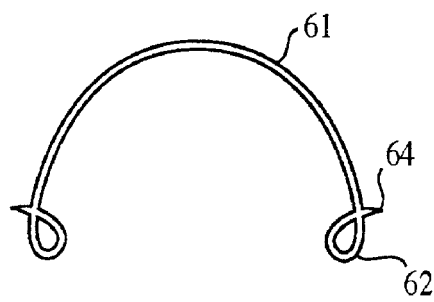
FIG. 5 is a schematic view of an embodiment of a closure device.

Referring to FIG. 5, in another embodiment, the closure device 61 can be an open strand defining an arc, which includes ends 64 with anchoring elements 62, which define loops. Once the anchoring elements 62 are positioned on the exterior of the blood vessel, the loops defined by the elements 62 prevent the ends 64 of the closure device 61 from reentering the blood vessel and secure the closure device 61 to the wall. The loops can be pressed into the vessel wall on implantation. Alternatively, the ends can be formed of a temperature effect shape memory metal, such that the ends are in a substantially straight condition for implantation but subsequently revert to a loop shape after being embedded in the vessel wall.

Figure 6:
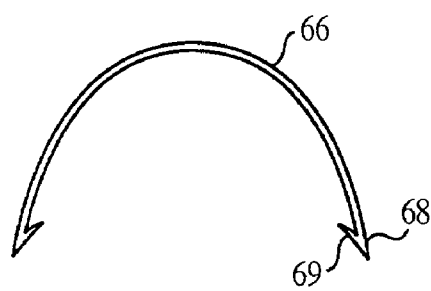
FIG. 6 is a schematic view of an embodiment of a closure device.

Referring to FIG. 6, the closure device 66 can alternatively include ends 68 with anchoring elements 69 configured with barbs, such that the ends 68 can penetrate the wall of the blood vessel and be prevented from reentering the blood vessel by the barbs of the fish hook-like anchoring elements 69.

Figure 7:
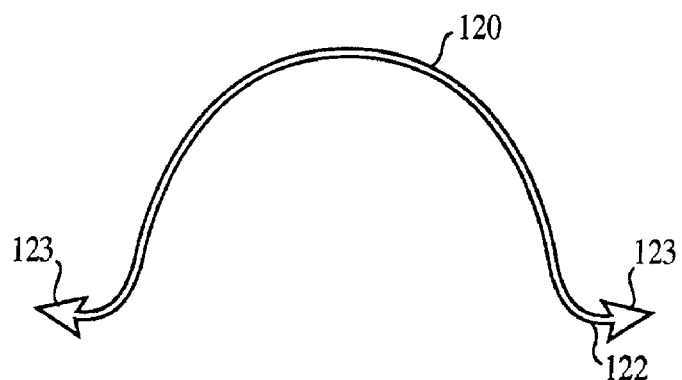
FIG. 7 is a schematic view of an embodiment of a closure device.

Referring to FIG. 7, the closure device can be an open strand 120 having flared ends 122 that terminate in barb elements 123. The ends 122 can penetrate the wall of the blood vessel and secure the strand 120 to the wall by the curvature of the flared ends 122. The barb elements are easily pushed into the vessel wall as the device is extended, but resist withdrawal from the wall as the device deflects inwardly.

Figure 8A:
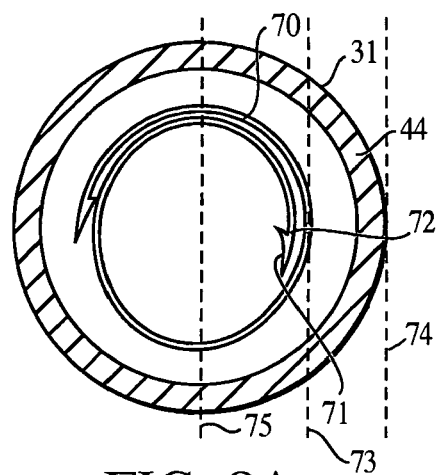
FIGS. 8A, 8B and 8C are radial cross-sectional views illustrating implantation of a closure device from within a vessel.
Figure 8B:
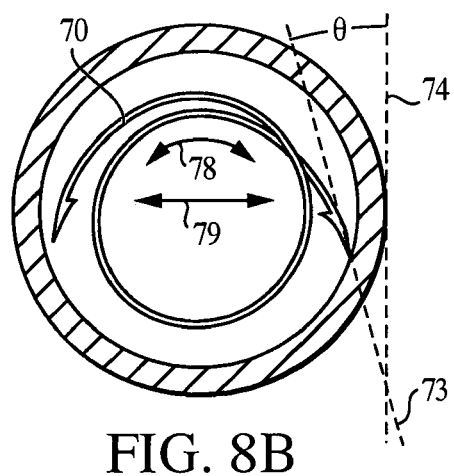
Figure 8C:
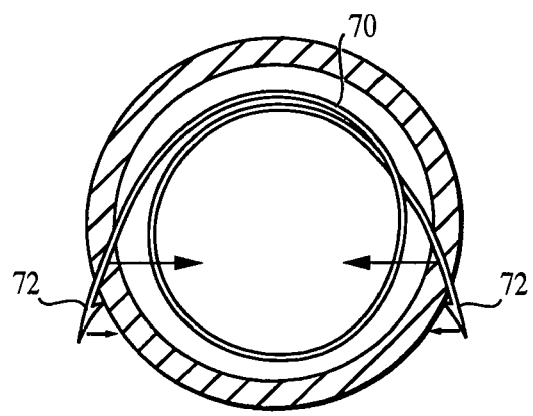

As shown in FIGS. 8A–8C, the closure device 70 can be a spiraled open strand to form a loop and a half or more, so that the ends 72 are positioned opposite one another, and include fish hook-like anchoring elements 71. Referring particularly to FIG. 8A, the closure device 70 is shown in a compacted condition, with the anchoring elements 71 oriented along a tangent line 73, which is substantially parallel to the center line 75 through the cross-section of the blood vessel, and parallel to a tangent 74, on the blood vessel wall. Referring particularly to FIG. 8B, as the closure device 70 is expanded by the expansion device (not shown), the strand can both stretch axially (arrow 78) and deform radially (arrow 79). The axial stretch does not fully accommodate the expansion. As a result, the free ends 72 of the strand are deflected such that the tangent line 73 defines an angle θ with respect to the tangent 74 on the vessel wall and thus penetrates the vessel wall. Referring to FIG. 8C, as the device 70 begins to contract, the ends 72 of the strand further penetrate the wall and deflect inwardly to contract the wall.

Figure 9:
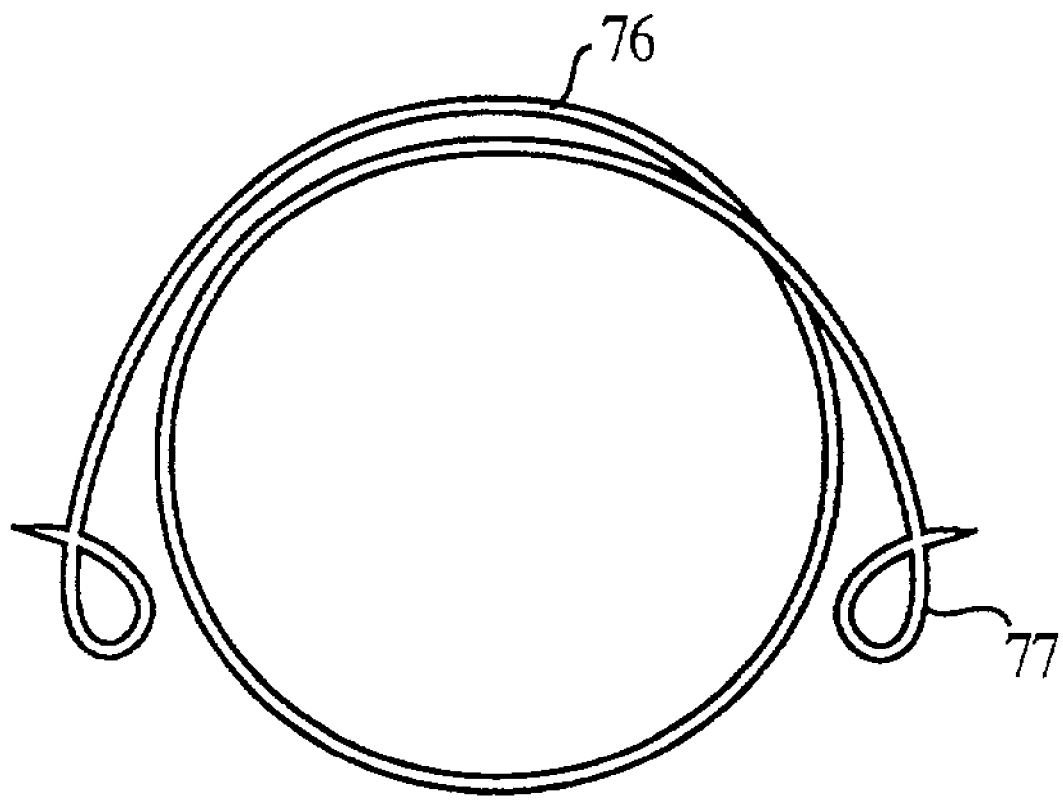
FIG. 9 is a schematic view of an embodiment of a closure device.

Referring to FIG. 9, the closure device 76 can be a spiraled open strand to form a loop and a half, so that the ends 72 are positioned opposite one another, and include anchoring elements 77 defining loops. Implantation of this device would be similar to implantation of the device shown in FIG. 8, as described above.

Figure 10:
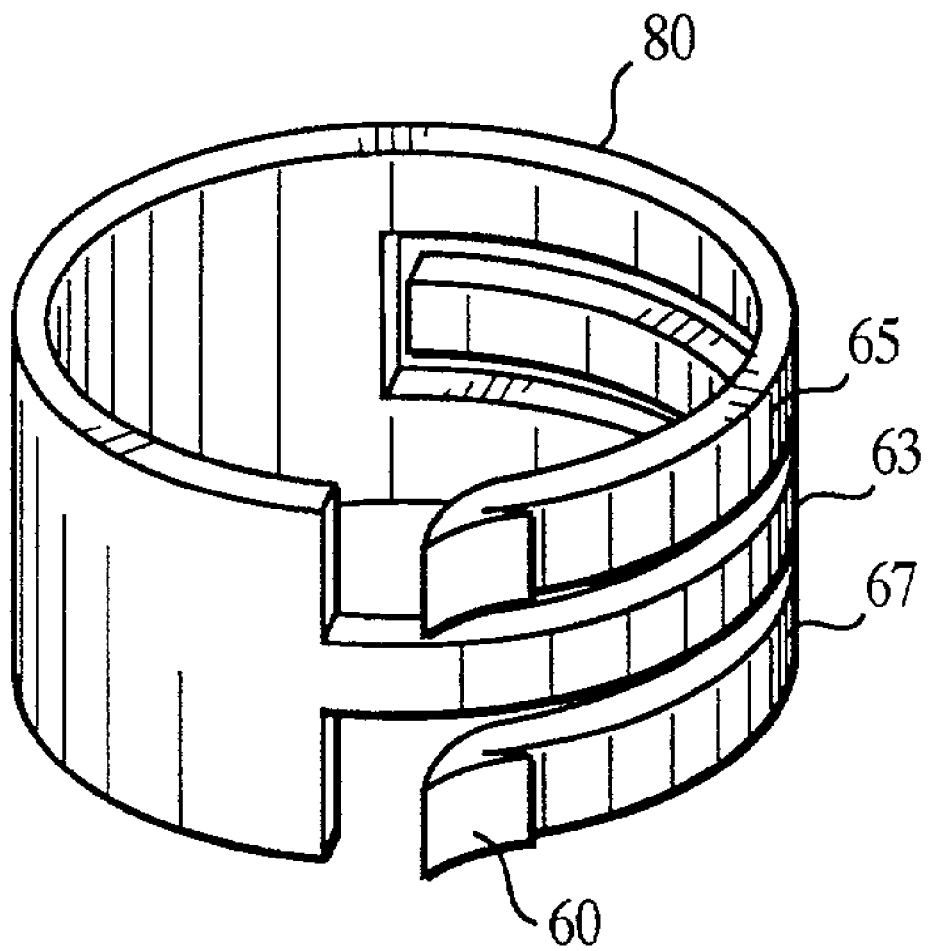
FIG. 10 is a schematic view of an embodiment of a closure device.

Referring to FIG. 10, the closure device 80 can be a strand in the shape of a thin, flat slotted band including three (or more) anchoring elements 60. The slotted band 80 can include an upper band 65, middle band 63 and lower band 67, where the upper band 65 and lower band 67 each include an anchoring element 60 on their distal ends on an opposite side of the band 80 from an anchoring element 60 formed at the distal end of the middle band 63. Expansion of the closure device 80 by an expansion device causes the anchoring elements 60 to penetrate the vessel wall. Upon contracting the expansion device, the band 80 attempts to contract to the smaller condition and, because the band 80 is secured to the vessel wall, contracts the cross-section of the vessel.

Figure 11:
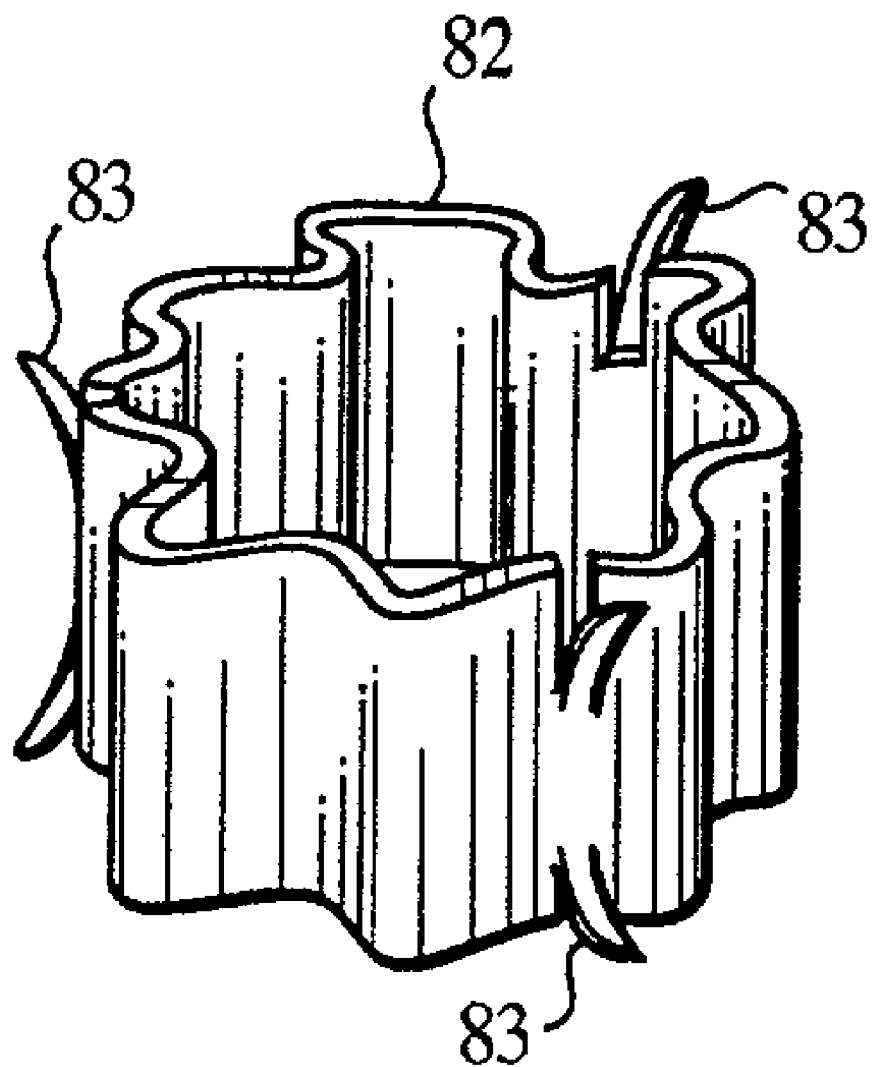
FIG. 11 is a schematic view of an embodiment of a closure device.

Referring to FIG. 11, in another embodiment, the closure device can be a closed, corrugated band 82. The band 82 includes anchoring elements 83 projecting from the exterior surface of the band. As the band 82 is expanded, the anchoring elements 83 penetrate the wall of the blood vessel. The anchoring elements 83 can be configured such that they lie flat while being transported through the vessel, and are caused to protrude from the band 82 by the expansion of the band 82 using an expansion device. When the expansion device is contracted, the band 82 attempts to contract to a smaller condition, and the anchoring elements 83 cause the cross-section of the vessel to contract.

Referring to FIGS. 12A–12D, the closure device can be a helical winding 85 having two or more anchoring portions 86 and having any number of helical turns, for example three turns as shown. Referring to FIG. 12A, the helical winding 85 can be transported to the treatment site within a vessel 31 using a catheter 88 having an expander 87 on the distal end. The treatment site is in close proximity to an incompetent venous valve 24. The helical winding 85 is mounted to the exterior of the expander 87 and can be held in place by any convenient manner, including, for example, a friction fit. Optionally, a protective sheath 89 can cover the expander 87 and helical winding 85 during transport and be removed once the treatment site is reached. Referring to FIG. 12B, the expander 87 is expanded and thereby expands the helical winding 85 from a small condition to a larger condition. The expander 87 is expanded until the anchoring portions 86 of the helical winding 85 penetrate the wall 44 of the vessel 31 and secure the helical winding 85 to the interior of the vessel 31. The helical winding 85 can have three anchoring portions 86 as shown in FIG. 12C, or more or less anchoring portions. The expander 87 is then contracted and the catheter 88 removed from the vessel 31, for example, in the same manner the catheter 88 was deployed. Referring to FIG. 12D, with the expander 87 no longer exerting pressure on the helical winding 85, the helical winding 85 tends to contract to the small condition, for example, due to elastic restoring forces or temperature-effect shape memory effect, thereby pulling the sides of the wall 44 inwardly and contracting the cross-sectional area of the vessel 31. With the helical winding 85 in place within the vessel 31, the cusps 38 of the valve 24 are pulled together so that the valve 24 can function competently to prevent antegrade flow within the vessel 31.

Figure 13A:
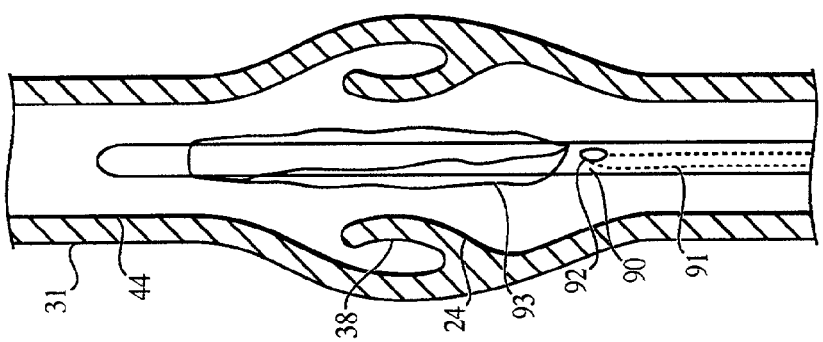
FIGS. 13A, 13B, 13C, 13D and 13E are longitudinal cross-sectional schematic views illustrating implantation of a closure device from within a vessel.
Figure 13B:
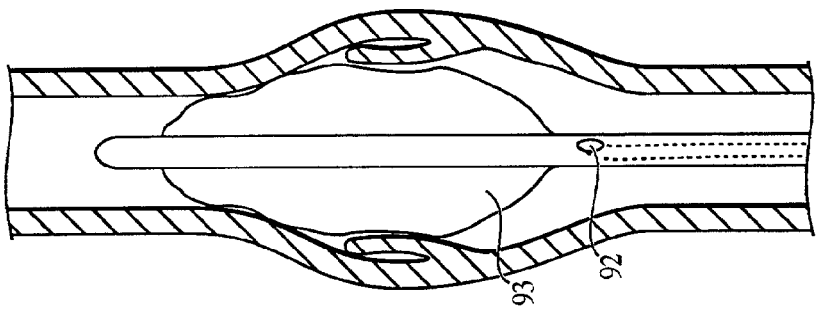
Figure 13C:
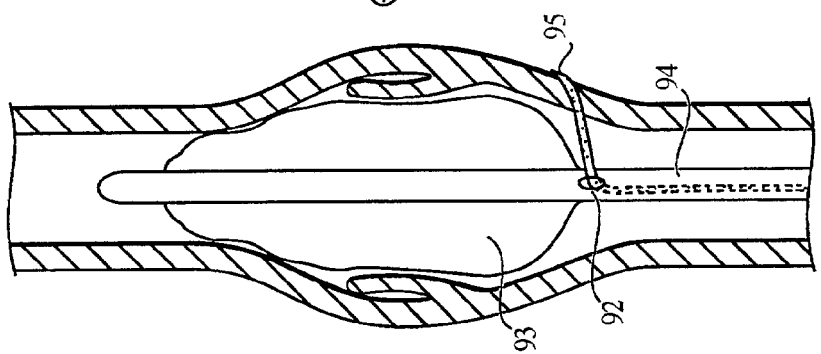
Figure 13D:
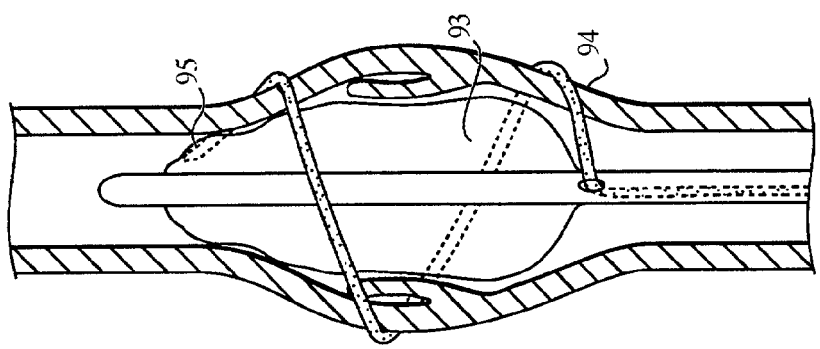
Figure 13E:
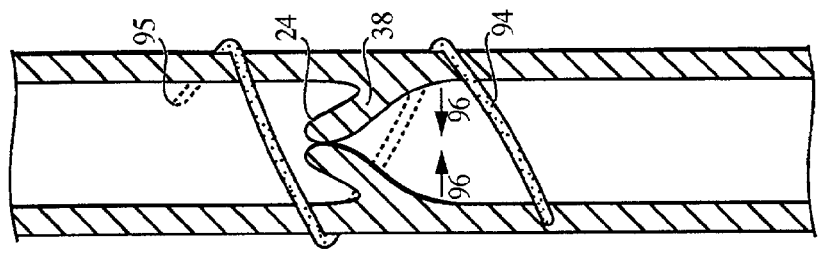

Referring to FIGS. 13A–13E, the closure device can be a helical winding 94 that is positioned about the exterior of a vessel 31 in the vicinity of an incompetent venous valve 24. Referring to FIG. 13A, a catheter 90 having an expander 93 on the distal end is transported to a treatment site with the expander 93 in a contracted state. The treatment site is at or near the incompetent venous valve 24. The catheter 90 includes a lumen 91 having an opening 92 at or near the base of the expander 93. Referring to FIG. 13B, at the treatment site the expander 93 is expanded to at least the interior dimension of the vessel 31. The helical winding 94 is formed of a shape-memory material and is passed through the catheter lumen 91 in a substantially straight position, as shown in FIG. 13C. The helical winding 94 is pushed through the opening 92, which opening 92 is configured such that the winding 94 is directed toward the wall 44 of the vessel 31. The winding 94 penetrates and is pushed through the wall 44. The shape-memory effect causes the winding 94 to revert to a helix as the winding is pushed from the catheter lumen 91, and rides along the outside of the vessel 31. Once the helical winding 94 has completely exited the catheter lumen 91 and is situated about the exterior of the vessel 31, the expander 93 is contracted and the catheter 90 is withdrawn from the vessel. The helical winding 94 is configured so that when the shape-memory effect causes the winding to revert to a helix, the helical winding 94 pulls the wall 44 of the vessel 31 inwardly, causing the cusps 38 to pull together so that the valve can function competently. The winding 94 can be held in place by friction.

Figure 14A:
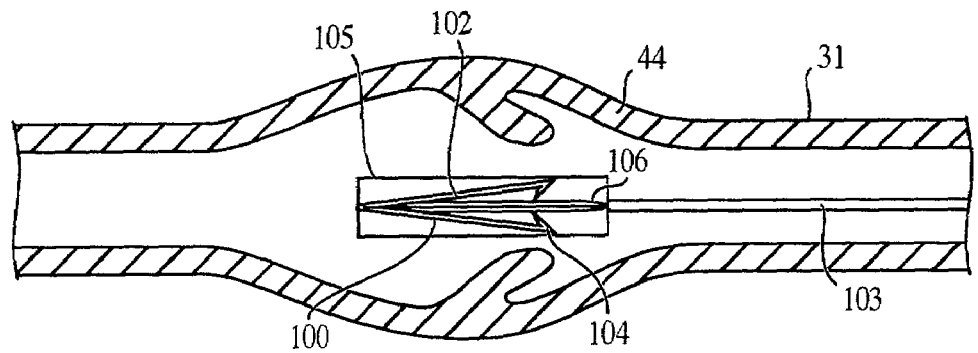
FIGS. 14A, 14B and 14C are longitudinal cross-sectional schematic views illustrating implantation of a closure device from within a vessel.
Figure 14B:
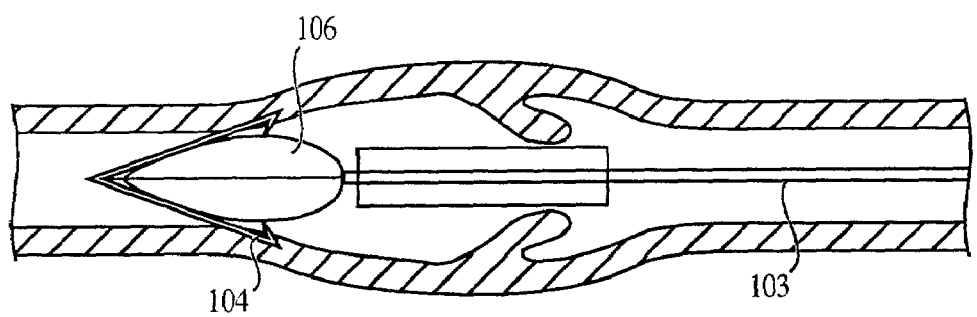
Figure 14C:
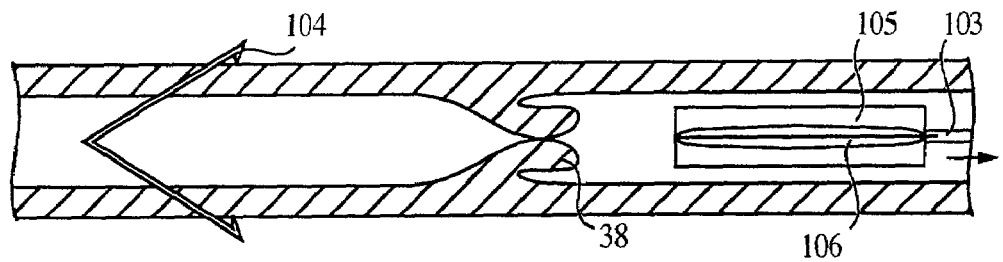

Referring to FIGS. 14A–14C, the closure device 100 can be an angular hinge-form with at least two linear legs 102. The closure device 100 can be transported in a compressed condition to a deployment site in the blood vessel by a delivery catheter 103 having a housing 105 for containing the closure device 100 in the compressed condition until the deployment site is reached. The device 100 can be pushed out of the housing 105 by the distal end of the catheter, which can be temporarily connected to the device 100, for example, by a threaded connection. Referring particularly to FIG. 14B, the device 100 will naturally expand upon being released from the confines of the housing 105. An expansion device 106, such as an inflatable balloon, on the distal end of the catheter 103 can be inflated to further expand the closure device 100 by spreading the legs 102 until the anchoring elements 104 penetrate the wall 44 of the blood vessel 41. The device 100 is then pulled in the direction of the catheter by the distal end of the catheter, which is still connected to the device 100. This movement causes the anchoring elements 104 to fully penetrate the wall of the blood vessel, and secure the device 100 to the vessel. The catheter is disconnected from the device 100 and removed from the vessel. The device 100 attempts to contract to a smaller condition, thus causing the cross section of the blood vessel to contract.

Referring to FIGS. 15A–15C, the expander can be a mechanical expander 135 including at least two coiled springs 128, 129 and having a two-part axial member including an outer tube 133 and an inner rod 134. The inner rod 134 is affixed to a first coil 129 and can rotate independently of the outer tube 133, which is affixed to a second coil 128. The mechanical expander 135 is used in conjunction with a closure device 125 configured to mount about the coils 128, 129. Each coil 128, 129 has an end 130, 131 configured to fit within a groove 127 formed on either end of the closure device 125. In this manner, the coils 128, 129 and closure device 125 are held together while the expansion device is transported to a treatment site. At the treatment site, the mechanical expander 135 is expanded to expand the closure device 125, thereby causing the anchoring portions 126 of the closure device 125 to penetrate a vessel wall, in a similar manner as described above.

The mechanical expander 135 expands by rotating the inner rod 134 to expand the first coil 129 and rotating the outer tube 133 to expand the second coil 128. The coils 128, 129 expand radially in opposite directions, exerting a radial force on the closure device 125, causing the anchoring portions 126 to penetrate a vessel wall. Once the closure device 125 is secured to the vessel wall, the mechanical expander 135 can be disengaged from the closure device 125 by sliding the mechanical expander 135 axially away from the closure device 125. The mechanical expander 135 is contracted by rotating the inner rod and outer tube in the opposite directions used for expansion, and is withdrawn from the vessel. Optionally, a retractable sheath can enclose the mechanical expander 135 and closure device 125 while positioning the assembly at the treatment site, which sheath is then retracted.

Figure 16A:
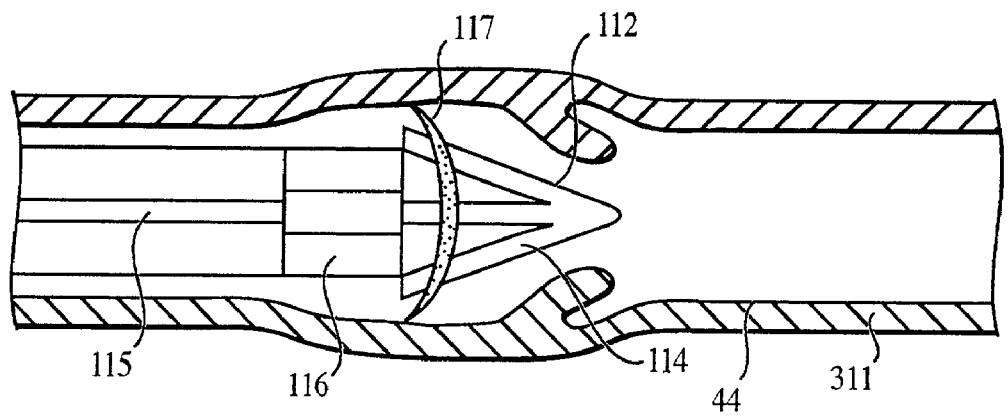
FIGS. 16A, 16B and 16C are longitudinal cross-sectional schematic views illustrating implantation of a closure device from within a vessel.
Figure 16B:
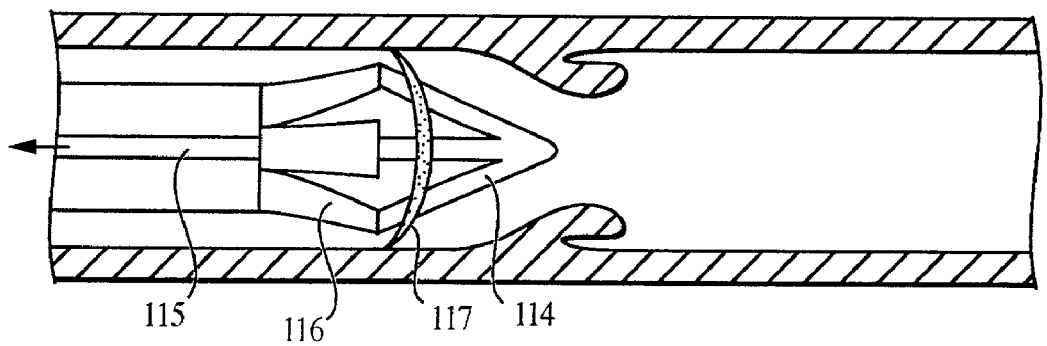
Figure 16C:
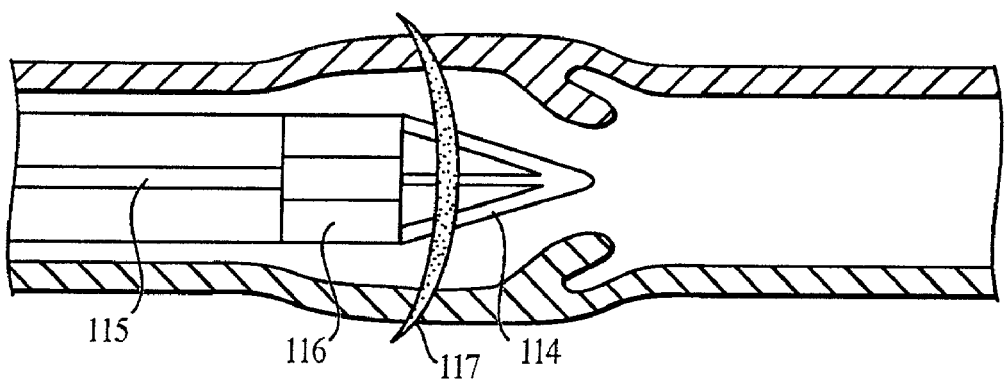

Referring to FIGS. 16A–16B, the expander can be a leveraging device 112 having at least two flexible legs 114, an axial member 115 and a splayed cuff 116. A closure device 117 can be mounted onto the exterior of the legs 114. At a deployment site, the axial member 115 can be pulled causing the legs 114 to press against the cuff 116. The force of the flexible legs 114 against the splayed cuff 116 causes the flexible legs 114 to expand outwardly and the splayed cuff 116 to fan out. The expansion of the circumference around the flexible legs 114 causes the closure device 117 to expand and anchor to the wall of the blood vessel 31, as described above. Once the closure device 117 is secured to the wall, the axial member 115 is pushed to release the pressure on the flexible legs 114, causing them to revert back to the original compressed condition. Similarly, with the force on the splayed cuff 116 removed, the cuff 116 recovers to the original state. The expansion device can then be retracted from the vessel.

Other embodiments are within the scope of the following claims. For example, a closure device may be used to treat vascular vessels at locations without a valve to constrict the vessel at a desired location and other body lumens outside the vascular system.

What is claimed is:

1. A method of treating a vessel of a vasculature, comprising:
    delivering a closure device into a lumen of the vessel of the vasculature, the closure device comprising a strand having a helical shape;
    positioning the strand while in a first cross-sectional condition about a body lumen of the vessel of the vasculature such that a portion of the strand penetrates the wall of the body lumen; and
    deforming the strand to a second cross-sectional condition smaller than the first cross-section condition such that the wall of the body lumen of the vessel of the vasculature is moved inwardly.

2. The method of claim 1, wherein the strand is positioned about the body lumen such that an end of the strand extends through the wall of the body lumen.

3. The method of claim 2, further comprising:
    disposing the strand on a catheter; and
    delivering the catheter into the body lumen.

4. The method of claim 3, further comprising:
    providing the strand on a catheter including an expansion member.

5. The method of claim 1, further comprising:
    positioning the strand about a valve structure of the vessel of the vasculature.

6. The method of claim 4, further comprising:
    positioning the strand about the expansion member, where the expansion member operates between a small cross-section and a large cross-section.

7. The method of claim 6, where positioning the strand about the expansion member comprises positioning the strand about an inflatable balloon.

8. The method of claim 6, where positioning the strand about the expansion member comprises positioning the strand about a mechanical expander.

9. The method of claim 6, where positioning the strand about the expansion member comprises positioning the strand about a leveraging device.

10. The method of claim 1, where deforming the strand to the smaller cross-section includes deforming the strand from a first cross-section condition to a larger cross-section condition; and deforming the strand from the larger cross-section condition to the smaller cross-section condition upon implantation in the body lumen adjacent a venous valve.

11. The method of claim 1, where positioning the strand about the body includes penetrating the wall of the body lumen with at least two anchoring portions disposed along the strand.

12. The method of claim 1, where positioning the strand about the body lumen includes penetrating anchoring portion of the strand through the wall of the body lumen in a large cross-section condition.

13. The method of claim 1, where delivering the closure device into the lumen includes delivering an arched closure device into the lumen.

14. The method of claim 1, where delivering the closure device into the lumen includes delivering a helical closure device into the lumen.

15. The method of claim 1, where deforming the strand includes changing the strand from a large cross-section to the smaller cross-section condition by elastic recovery forces.

16. The method of claim 1, where deforming the strand includes changing the strand from a large cross-section to the smaller cross-section condition by thermal shape-memory effect.

* * * * *